US 6,313,275 B1

(12) United States Patent
Mülhaupt et al.

(10) Patent No.: US 6,313,275 B1
(45) Date of Patent: Nov. 6, 2001

(54) AZOIC COMPOUNDS FUNCTIONALIZED WITH HETEROCYCLES

(75) Inventors: Rolf Mülhaupt; Martin Baumert, both of Freiburg; Michael Geprägs, Lambsheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/582,781

(22) PCT Filed: Sep. 11, 1998

(86) PCT No.: PCT/EP98/05806

§ 371 Date: Jul. 3, 2000

§ 102(e) Date: Jul. 3, 2000

(87) PCT Pub. No.: WO99/37629

PCT Pub. Date: Jul. 29, 1999

(30) Foreign Application Priority Data

Jan. 23, 1998 (DE) .............................. 198 02 335

(51) Int. Cl.⁷ .............................. C07D 263/10; C08F 4/04
(52) U.S. Cl. .................... 534/751; 534/799; 525/204; 526/204; 526/218.1
(58) Field of Search ................. 534/751, 799; 526/204, 218.1; 525/204

(56) References Cited

U.S. PATENT DOCUMENTS

| 2,901,473 | 8/1959 | Steinemann | 534/710 |
| 3,914,340 | * 10/1975 | Dekking | 525/267 |
| 4,569,979 | * 2/1986 | Harada et al. | 526/218.1 |
| 4,990,600 | * 2/1991 | Tanaka et al. | 534/751 |
| 5,124,431 | * 6/1992 | Ohta et al. | 528/183 |

FOREIGN PATENT DOCUMENTS

| 356 026 | 2/1990 | (EP) . |
| 682 758 | 9/1997 | (EP) . |

OTHER PUBLICATIONS

Gupta et al., Chemical Abstracts, 84:17803, 1976.*
Murashige, Chemical Abstraacts, 112:78200, 1990.*
Narita et al., Chemical Abstracts, 116:106880, 1992.*
Usui, Chemical Abstracts, 119:162086, 1993.*
Fujama et al., Chemical Abstracts, 125:87497, 1996.*
Lehrbuch der Org. Chem. Morrison, 1984,1110–111.
Mac.Rap.Com. 18, 787–794(1997) Baumert et al.
Mak.Chem.Rap.Com. 12, 435–438(1991)Sivaram et al. 435–439.
Patent Abstracts of Japan, Abstract of JP 06–93100, Apr. 5, 1994.
Chemical Abstracts, 96:199667, 1982.

* cited by examiner

Primary Examiner—Fiona T. Powers
(74) Attorney, Agent, or Firm—Keil & Weinkauf

(57) ABSTRACT

Azo compounds of the formula (I)

$$Y-N=N-X-C(=N-)(Z-)(C(R^a)(R^{a'}))_k$$ (I)

are functionalized with heterocycles.

14 Claims, No Drawings

AZOIC COMPOUNDS FUNCTIONALIZED WITH HETEROCYCLES

The present invention relates to heterocycle-functionalized azo compounds of the formula (I)

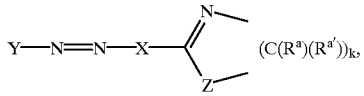

where:

Y is $C_1$–$C_{20}$-alkyl, $C_6$–$C_{14}$-aryl, $C_6$–$C_{14}$-aryl substituted with functional groups based on the nonmetallic elements of groups IVA, VA, VIA or VIIA of the Periodic Table, $C_3$–$C_{10}$-cycloalkyl, aralkyl having from 1 to 10 carbon atoms in the alkyl radical and from 6 to 14 carbon atoms in the aryl radical, $C_1$–$C_{20}$-alkyl substituted with functional groups based on the nonmetallic elements of groups IVA, VA, VIA or VIIA of the Periodic Table, or a radical of the formula (II)

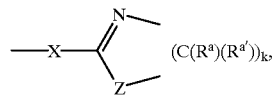

where, as in formula (I):

$R^a$ and $R^{a'}$, independently of one another, are hydrogen, $C_1$–$C_{20}$-alkyl, $C_6$–$C_{14}$-aryl, aralkyl having from 1 to 10 carbon atoms in the alkyl radical and from 6 to 14 carbon atoms in the aryl radical, or $C_3$–$C_{10}$-cycloalkyl, or, but not both simultaneously, functional groups based on the non-metallic elements of groups IVA, VA, VIA or VIIA of the Periodic Table, Z is oxygen, sulfur or —N(R')—, X is —(C($R^b$) ($R^{b'}$))$_l$— or [=N]—(C($R^b$) ($R^{b'}$))$_m$—A—(C($R^b$) ($R^{b'}$))$_n$—(E)$_p$—, where $R^b$ and $R^{b'}$, independently of one another, are defined as for $R^a$ and $R^{a'}$, A is —C(O)O—, —O—, —S—, —C(O)N(R")—, —N(R")—, —C(O)—, —C (R")=N—, E is substituted or unsubstituted $C_6$–$C_{14}$-arylene, R' and R" are hydrogen, alkyl, aryl or aralkyl, k is 2 or 3, l is an integer from 1 to 24, m and n are integers from 0 to 12, and p is 0, 1, 2 or 3, where m+n≧1 and n+p≧1.

The invention also relates to the use of the azo compounds mentioned above as initiators for the free-radical polymerization of olefinically unsaturated compounds, and also to a process for preparing heterocycle-functionalized azo compounds. The invention relates, furthermore, to processes for preparing (co)polymers containing heterocyclic end groups, and also to a process for preparing graft copolymers and block copolymers, and to the resultant (co)polymers, block copolymers and graft copolymers and the use of these for producing films, fibers and moldings. Finally, the invention relates to the use of the (co)polymers for preparing block copolymers and graft copolymers.

The suitability of azo compounds as initiators for free-radical reactions, and in particular also for free-radical polymerization of olefinically unsaturated compounds, has been known for a long time (cf. R. T. Morrison R. N. Boyd, Lehrbuch der Organischen Chemie, Verlag Chemie, 3rd impression of the 2nd edition, 1984, pages 1110 and 1111). Azoisobutyronitrile (AIBN) has exceptional importance among these compounds as a free-radical chain initiator. A consequence of the mechanism of initiation is generally that at least a fragment of the azo compound becomes incorporated as a terminal member of the polymer chain. As described in EP-A 0 356 026, this property of azo initiators has already been utilized to tie an amide function containing aromatic and/or nitrogen-containing ring systems to the terminal member of a polymer chain. It is claimed in EP-A 0 356 026 that the resultant polymer is suitable for downstream reactions such as the formation of block copolymers and/or graft copolymers. The application mentioned does not provide further details on this topic. In addition, the yields obtained in the polymerization of, for example, acrylonitrile are much too low for the process to be technically and economically acceptable.

It is apparent from JP-A 08225504 that the azo compounds disclosed in EP-A 0 356 026, e.g. 2,2'-azobis[N-(isopropyl)-2-methylpropionamide], are possible initiators for free-radical polymerization of styrene and acrylonitrile. There is no report of downstream reactions. Carboxyl-terminated homopolymers and copolymers of styrene, and their preparation using dicarboxylic-acid-functionalized azo initiators in the presence of 2,2,6,6-tetramethyl-1-piperidyloxyl radical, are proposed by Baumert and Mülhaupt in Macromol. Rapid Commun. 1997, 18, 787–794, but without describing terminal groups of other types. Reactions leading to downstream products are likewise not described. EP-A 0 792 869 makes reference to azo initiators which are soluble in organic solvents and retain their activity at high temperatures. This object is achieved by means of 2,2'-azobisamides with amido substituents which have at least two carbon atoms. It is not disclosed whether these compounds give polymeric products with which downstream reactions can be carried out, and this is also not within the subject matter of EP-A 0 792 869.

Sivaram et al. (Macromol. Rapid Commun. 1991, 12, 435–438) use the carbanion of 2-methyl-1,3-oxazoline as an initiator for the anionic polymerization of methyl acrylate. The authors propose that the oxazoline group incorporated into the polymer chain in this way be used for preparing graft copolymers. There is no disclosure of further details or of corresponding descriptions of experiments. A disadvantage of the process of Sivaram et al. is that the synthesis of oxazoline-terminated (meth)acrylates requires much technical resource, and gives satisfactory results only at very low temperatures, too low to be economically acceptable. A further disadvantage is that the oxazoline group can only be incorporated into those polymers which are obtainable by anionic polymerization, i.e. primarily acrylates and methacrylates.

It would therefore be desirable to have access to initiator systems which can be used to incorporate a reactive functional group into a polymer chain without restriction to a limited number of polymerizable monomers.

It is an object of the present invention to develop initiator systems in which the disadvantages described are absent or are present only to a subordinate extent, which are easy to obtain, and which can readily be used for specific incorporation into a wide variety of polymers of a functional group, which does not undergo side and/or coupling reactions during the polymerization process but is suitable for downstream reactions.

We have found that this object is achieved by means of the heterocycle-functionalized azo compounds described at the outset. The invention also provides a process for preparing azo compounds of this type, and also their use as initiators for the free-radical polymerization of olefinically unsaturated compounds. It further provides a process for preparing copolymers containing heterocyclic end groups, and also a process for preparing graft copolymers and block copolymers. It likewise provides the (co)polymers, block copolymers and graft copolymers obtainable by the processes, and the use of these for producing films, fibers and moldings. Finally, it provides the use of the (co)polymers for preparing block copolymers and graft copolymers.

The novel azo compounds have at least one five- or six-membered heterocycle having, integrated into its ring, at least two, 1,3-positioned, heteroatoms, one of these being nitrogen. The other heteroatoms may be oxygen, sulfur or nitrogen. In the compounds of the formula (I), Z is preferably oxygen, sulfur or nitrogen, in particular oxygen. Examples of suitable ring systems are oxazoline, thiazoline and imidazoline, the heterocycle generally being bonded to the skeleton of the azo compound via the 2-position. Preference is given to 1,3-oxazoline and 1,3-thiazoline, but in particular 1,3-oxazoline.

Possible radicals $R^a$ and $R^{a'}$ in compounds of the formula (I) are very generally hydrogen, linear or branched $C_1$–$C_{20}$-alkyl, in particular $C_1$–$C_{10}$-alkyl, such as methyl, ethyl, isopropyl or tert-butyl, $C_6$–$C_{14}$-aryl, in particular $C_6$–$C_{10}$-aryl, such as phenyl, aralkyl having from 1 to 10 carbon atoms in the alkyl radical and from 6 to 14 carbon atoms in the aryl radical, preferably having from 1 to 6 carbon atoms in the alkyl radical and from 6 to 10 carbon atoms in the aryl radical, for example benzyl, substituted or unsubstituted $C_3$–$C_{10}$-cycloalkyl, preferably $C_5$–$C_8$-cycloalkyl, such as cyclopentyl or cyclohexyl, or, not simultaneously, functional groups based on the nonmetallic elements of groups IVA, VA, VIA or VIIA of the Periodic Table, for example the carboxylic acid, ester, amide, nitrile or triorganosilyl group, the primary, secondary or tertiary amino or phosphino group, the hydroxyl or alkoxy group, or fluorine or chlorine. Particular preference is given to hydrogen or methyl. Hydrogen is particularly preferred. In a particularly preferred embodiment, the substituents $R^a$ and $R_a'$ are hydrogen in the α position to Z.

The novel azo compounds may also have identical or different radicals on the nitrogen atoms of the azo group. One radical or both radicals may therefore be substituted with one or more nitrogen-containing heterocycles. If both radicals are substituted with one or more heterocycles, these may be completely identical or else differ to some extent from one another. Formula (I) therefore includes both symmetrical and asymmetrical azo compounds.

If only one radical of the azo compound carries a heterocycle as in formula (I), the other radical Y in (I) may be linear or branched $C_1$–$C_{20}$-alkyl, preferably $C_1$–$C_{10}$-alkyl, such as methyl, ethyl, isopropyl or tertbutyl, $C_6$–$C_{14}$-aryl, preferably $C_6$–$C_{10}$-aryl, such as phenyl, $C_6$–$C_{14}$-aryl substituted with functional groups based on the nonmetallic elements of groups IVA, VA, VIA or VIIA of the Periodic Table, preferably $C_6$–$C_{10}$-aryl, such as tolyl, anisyl, trifluoromethylphenyl, nitrophenyl or fluorophenyl, $C_3$–$C_{10}$-cycloalkyl, preferably $C_5$–$C_8$-cycloalkyl, such as cyclopentyl or cyclohexyl, aralkyl having from 1 to 10 carbon atoms in the alkyl radical and from 6 to 14 carbon atoms in the aryl radical, preferably having from 1 to 6 carbon atoms in the alkyl radical and from 6 to 10 carbon atoms in the aryl radical, for example benzyl, or $C_1$–$C_{20}$-alkyl substituted with functional groups based on the nonmetallic elements of groups IVA, VA, VIA or VIIA of the Periodic Table, preferably linear or branched $C_1$–$C_{10}$-alkyl, e.g. substituted with a triorganosilyl, nitrile, carboxylic acid, ester, amide, amino, phosphino, hydroxyl, alkoxy or halo group. In a particularly preferred embodiment, the radical Y of the azo compound (I) has the formula (II)

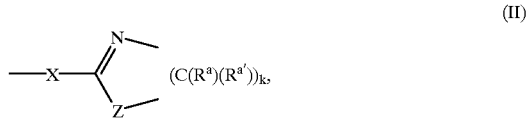

(II)

where the general and preferred definitions of X, Z, $R^a$, $R^{a'}$ and k are as for formula (I).

Particularly suitable azo compounds (I) are those in which the radical of formula (II) is identical with the radical carrying the heterocycle in (I).

The heterocycle is not generally immediately adjacent to the azo group. There is preferably a spacer unit X between the azo group and the heterocycle. These are mostly a hydrocarbon chain having from 1 to 24 members and the formula $—(C(R^b)(R^{b'}))_l—$ or a multimembered chain of the formula $[=N]—(C(R^b)(R^{b'}))_m—A—(C(R^b)(R^{b'}))_n—(E)_p—$, where m and n are integers from 0 to 12 and m+n≧1. E is substituted or unsubstituted $C_6$–$C_{14}$-arylene, which may be incorporated into the spacer unit via vicinal or via nonvicinal carbon atoms of the aromatic system. This may, for example, be 1,2-, 1,3- or 1,4-phenylene. Possible substituents are in particular all those which have also been listed for the substituted $C_6$–$C_{14}$-aryl radical Y. The spacer segment may comprise an arylene group, e.g. 1,4-phenylene or 1,5-naphthylene, or more than one linked arylene group (p=1, 2, 3 or 4), for example 1,1'-bisphenylene. If n=0, the spacer segment between the functional group A and the heterocycle consists exclusively of an arylene group, e.g. a 1,4-phenylene unit. In contrast, this segment is simply a substituted or unsubstituted hydrocarbon chain in cases where p=0, i.e. n+p≧1, n and p being integers. The nitrogen atom placed in square brackets is not a part of the spacer unit X, but is the point at which the azo group begins. The method chosen for depicting the formula is intended exclusively to make clear the manner of linkage.

The radicals $R^b$ and $R^{b'}$ may generally be defined by the general definition of the radicals $R^a$ and $R^{a'}$. This applies in particular to the radicals $R^b$ and $R^{b'}$ which are not situated in the position α to the azo group.

The radicals $R^b$ and $R^{b'}$ in the position α to the azo function are preferably simply linear $C_1$–$C_{20}$-alkyl, in particular $C_1$–$C_{10}$-alkyl, preference being given to methyl, ethyl, n-propyl, n-butyl, n-pentyl, n-hexyl, n-heptyl and n-octyl. Methyl is particularly preferred among these linear alkyl radicals.

Particular preference is also given to an electron-withdrawing group positioned α to the azo function. Examples of possible groups are the nitrile, trifluoromethyl and ester groups. Among these last-named groups, the nitrile group is particularly suitable.

The spacer unit X may consist either of a purely hydrocarbon chain or else of a hydrocarbon chain which is interrupted by one or more functional groups A, such as carboxy, amido, oxo, thio, imino, amino or keto. Particular groups are carboxy, amido, keto and oxo, the carboxy function being particularly preferred. Carboxy functions (=ester groups) may therefore be an integral part of one or both spacer units X in (I). The spacer unit X is preferably interrupted by only one functional group.

The number of members of a hydrocarbon chain in X lying between the azo group and the functional group generally amounts to an integer m in the range from 0 to 12, preferably from 0 to 7. The spacer unit X likewise generally has from 0 to 12 members in a hydrocarbon chain, preferably from 0 to 7 members, between the functional group A and the heterocycle. Examples of preferred substituents for the hydrocarbon chain of the spacer unit X, in as far as the position α to the azo group is not concerned, are hydrogen, linear or branched $C_1$–$C_{10}$-alkyl, in particular methyl, ethyl, propyl or butyl, $C_6$–$C_{14}$-aryl, in particular $C_6$–$C_{10}$-aryl, such as phenyl, or aralkyl having from 1 to 6 carbon atoms in the alkyl moiety and from 6 to 10 carbon atoms in the aryl moiety, for example benzyl. Among the radicals mentioned above, particular preference is given to hydrogen, methyl, phenyl and benzyl, but in particular to hydrogen.

The radicals R', R" and R'" may be hydrogen, linear or branched, substituted or unsubstituted, $C_1$–$C_{20}$-alkyl, such as methyl, ethyl, n-propyl, isopropyl, n-butyl, isobutyl, tert-butyl, n-pentyl or n-hexyl, substituted or unsubstituted $C_6$–$C_{14}$-aryl, such as phenyl, naphthyl, tosyl or anisyl, or aralkyl having from 1 to 10 carbon atoms in the alkyl moiety and from 6 to 14 carbon atoms in the aryl moiety, for example benzyl. Alkyl radicals here include $C_3$–$C_{10}$-cycloalkyl, such as cyclopropyl or cyclohexyl. The same applies to the radicals $R^b$, $R^{b'}$, $R^c$ and $R^{c'}$.

In a preferred embodiment, the novel azo compounds have the following formula (I)

(I)

where:

$R^a$ and $R^{a'}$ are hydrogen or methyl, in particular hydrogen,

X, independently of one another, are [=N]—((C($R^b$)($R^{b'}$)) (C($R^c$)($R^{c'}$))$_{l-1}$)— or [=N]—((C($R^b$)($R^{b'}$)) (C($R^c$)($R^{c'}$))$_{m-1}$)—A—(C($R^c$)($R^{c'}$))$_n$—(E)$_p$—, where A is —C(O)O—, —C(O)—, —O—, —C(O)N(R")—, in particular —C(O)O—, E is substituted or unsubstituted $C_6$–$C_{14}$-arylene, in particular 1,4-phenylene, $R^b$ is $C_1$–$C_{10}$-alkyl, in particular methyl, $R^{b'}$ is —CN, —CF$_3$, —CO$_2$R'", in particular —CN, R" and R'" are hydrogen, alkyl, aryl or aralkyl, $R^c$ and $R^{c'}$ are hydrogen, $C_1$–$C_{10}$-alkyl, preferably methyl, ethyl, propyl or butyl, $C_6$–$C_{10}$-aryl, in particular phenyl, or alkylaryl having from 1 to 6 carbon atoms in the alkyl moiety and from 6 to 10 carbon atoms in the aryl moiety, preferably benzyl; hydrogen is particularly preferred, l is an integer from 1 to 16, preferably from 1 to 6, m and n are integers from 0 to 12, preferably from 0 to 7, and p is 0, 1, 2 or 3, where m+n≧1 and n+p≧1.

Examples of particularly preferred azo compounds which may be mentioned are:

2,2'-azobis[2-(1,3-oxazoline) propane],
2,2'-azobis[3-(1,3-oxazoline)pentane],
2,2'-azobis[2-(1,3-oxazoline) butane],
2,2'-azobis[1-(1,3-oxazoline)phenylethane],
the 5-(1,3-oxazolin-2-yl)pentyl ester of 4,4'-azobis-4-cyanopentanoic acid and also
the 5-(1,3-oxazolin-2-yl)pentyl ester of 4,4'-azobis-4-cyanohexanoic acid.

Surprisingly, the novel azo compounds (I) have been found to be accessible via an intramolecular ring-closure reaction from open-chain precursor compounds, suitable compounds for this having the formula (IIIa)

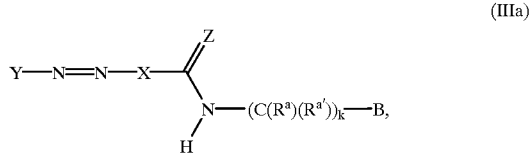

(IIIa)

where the general and preferred definitions of X, Y, Z, $R^a$ and $R^{a'}$, and also k, can be as described above under (I). In particular, Y may also be a radical of the formula (IV)

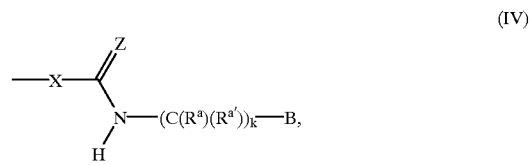

(IV)

where the definitions of X, Z, $R^a$ and $R^{a'}$ and also k, can be as for formula (IIIa).

The radical B in (IIIa) and (IV) is a leaving group which can readily be substituted by a halide in a halogenation reaction, for example hydroxyl, mesyl, tosyl, brosyl or trifluoromethyl-sulfonyl. Compounds of the formula (IIIa) are generally converted in a polar aprotic solvent, using, for example, thionyl chloride, thionyl bromide or sulfuryl chloride as halogenating agent, into the corresponding halide, the intermediate product (IIIb) in the preparation of the azo compounds (I); B in this product is halogen. It is also possible to complete the halogenation through treatment with a phosphorus trihalide, such as phosphorus tribromide, or also with triphenylphosphine and a halogen, such as chlorine or bromine, and/or with a tetrahalo carbon compound, such as carbon tetrachloride. Suitable solvents, inter alia, are polar aprotic liquid media, such as dichloromethane, chloroform, acetonitrile and dimethyl sulfoxide. Among these, use is particularly frequently made of dichloromethane. The substitution reaction is generally carried out at from −20 to 100° C., preferably from −10 to 60° C., over a period of from about 2 to 40 hours, preferably from 15 to 20 hours. It is advisable to use an excess of the halogenating agent in order to achieve complete conversion with a reaction time which is still acceptable in practice. A three- to ten-fold excess has proven suitable. A five-fold excess of halogenating agent usually gives satisfactory results. To isolate the intermediate product (IIIb) in which B is halide, preferably chloride, bromide or iodide, it is usually sufficient to separate insoluble constituents from the reaction mixture, for example by filtration, and to remove solvent from the resultant solution. The starting compounds (IIIa) are commercially available, for example as the commercial product VA 086 from Wako Chemicals.

The intramolecular ring-closure is brought about by treating the halogenated compounds (IIIb) with a base at from 0 to 50° C., preferably from 15 to 35° C., for from about 0.5 to 10 days, preferably from 4 to 6 days. Polar protic solvents have proven to be particularly suitable reaction media. Low-molecular-weight alcohols, such as methanol, ethanol or isopropanol may be mentioned as examples. Use of an equimolar amount of base, based on the functionality B in (IIIb) is generally sufficient for a successful reaction, but preference is nevertheless given to an excess of base. A two- to ten-fold molar excess of base is therefore suitable, based on the functionality B in (III). Possible bases are in principle any compound of this class having a $pK_a$ greater than 10. Particularly advantageous bases are ammonium hydroxide, alkali metal or alkaline-earth metal hydroxides, such as lithium hydroxide, sodium hydroxide, magnesium hydroxide or calcium hydroxide, or also mixtures of these. Potassium hydroxide is particularly preferred.

A particularly preferred embodiment of the novel process uses starting compounds of the formula (IIIa) in which B is not hydroxyl, but is mesyl, tosyl, brosyl or trifluoromethylsulfonyl, and the ring-closure reaction is brought about by direct base treatment, as described, omitting the halogenation step, thus obtaining compounds of the formula (I).

On the other hand, it is also possible to obtain compounds of the formula (I), in which the chain segment A is —C(O)O— by reacting a carboxylic-acid-carrying azo group with a compound with alcohol functionality and containing the heterocycle.

For example, a compound of the formula (V)

$$Y-N=N-(C(R^b)(R^{b'})_m-CO_2H \quad (V)$$

may be reacted with a compound of the formula (VI)

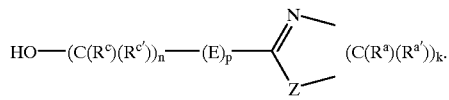

The substituents and indices are as defined under (I). Examples of suitable compounds (V) are 4,4'-azobis-4-cyanopentanoic acid and 4,4'-azobis-4-cyanohexanoic acid. Examples of suitable compounds (VI) are 2-(hydroxypentyl)-1,3-oxazoline and 1-hydroxy-4-(2-(1,3-oxazoline)benzene.

In the embodiment involving esterification, (I) is most suitably prepared in a polar aprotic solvent, preferably in the presence of a compound which removes water, such as dicyclohexylcarbodiimide, present in if possible an at least equimolar amount based on the molar amount of acid function. Particularly preferred polar aprotic solvents are dichloromethane, chloroform, tetra- hydrofuran, dioxane, dimethylsulfoxide and mixtures of these. The reaction is usually carried out at from −20 to 40° C., preferably from −5 to 20° C. It has proven advantageous for the reactants to be in contact for from about 0.5 to 10 hours, preferably from 2 to 5 hours. Simple filtering of the reaction mixture, if desired with the help of a filtration aid, such as alumina or silica gel, and removal of the solvent, gives compounds of the formula (I), which may be used per se, i.e. without further purification, as initiators for free-radical polymerization. Compounds of the formulae (V) and (VI) are commercially available.

The novel azo compounds of the formula (I) are suitable as initiators for the free-radical polymerization of olefinically unsaturated compounds. Either homo- or else copolymers are obtainable, these being jointly termed (co) polymers; for the purposes of the present invention, (co) polymers also includes oligomers.

The novel initiator may in principle be used for any unsaturated monomer capable of free-radical polymerization, including diene monomers, such as butadiene and isoprene. Other examples are $C_8$–$C_{20}$-vinylaromatics, such as styrene, α-methylstyrene, 4-methylstyrene or divinylbenzene, $C_3$–$C_{10}$-vinylcyanides, such as acrylonitrile or methacrylonitrile, $C_3$–$C_{20}$-(meth) acrylates, such as methyl acrylate, ethyl acrylate, glycidyl acrylate, dicyclopentadienyl acrylate, lauryl acrylate, n-butyl acrylate, isobutyl acrylate, 2-ethylhexyl acrylate, butyl methacrylate, 2-ethylhexyl methacrylate, lauryl methacrylate, glycidyl methacrylate, or methyl methacrylate, vinyl halides, such as vinyl chloride, vinylidene chloride, vinylidene fluoride or tetrafluoroethylene, $C_3$–$C_{14}$-vinyl esters or $C_3$–$C_{14}$-vinylamides, such as vinyl formate, vinyl acetate or vinylformamide, $C_2$–$C_{14}$-vinylsulfonic acids, such as vinylsulfonic acid or 4-vinylphenyl-sulfonate, vinylamines having at most 20 carbon atoms, such as vinyl amine or allyl amine, N-vinylpyrrolidone, vinylpiperidine, vinylpyridine or 1-vinylimidazole, or the dimethyl or -n-butyl esters of maleic acid, or derivatives of α,β-unsaturated $C_3$–$C_{20}$ aldehydes or of α,β-unsaturated $C_3$–$C_{20}$ alcohols, for example acrolein, crotonaldehyde, allyl alcohol or crotyl alcohol. It is also possible to use any desired mixture of the compounds mentioned above. Particularly suitable compounds are styrene, acrylonitrile, glycidyl methacrylate, methyl methacrylate and dicyclopentadienyl acrylate, n-butyl acrylate, 2-ethylhexyl acrylate, vinyl chloride, and also mixtures of these. The novel initiator has proven particularly successful in polymerizing butyl acrylate, 2-ethylhexyl acrylate, glycidyl methacrylate, styrene or acrylonitrile, and also for any desired mixture of these compounds.

The novel homo- and copolymers have at least one end group of the formula (VII)

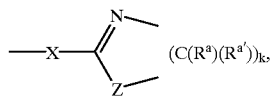

where the substituents and indices are defined as under formula (I). The polymer chains prepared using compound (I) as free-radical chain initiator therefore have a reactive terminal heterocycle.

The conventional free-radical polymerization may be carried out by commonly encountered methods, for example as described by B. Giese, Angew. Chem., 1983, 95, p. 771. Examples of possible methods are solution polymerization, bulk polymerization, suspension polymerization and emulsion polymerization. The molar ratio of monomer to initiator compound (I) may be varied over a wide range, and depends both on the compounds used and on the product parameters desired. It is generally in the range from 10:1 to 1,000,000:1, preferably in the range from 100:1 to 10,000:1. The polymerization is generally initiated thermally, i.e. the polymerization mixture is brought to a temperature in the range from −50 to 160° C., preferably from 20 to 130° C. and in particular in the range from 50 to 90° C. The lower limits of these ranges generally correspond to the decomposition temperature of the initiator used. The pressure for the polymerization reaction is generally in the range from 0.1 to 100 bar, in particular in the range from 1 to 70 bar. The polymerization time is usually in the range from 1 to 10 hours, preferably in the range from 2 to 5 hours. The polymerization is frequently carried out in bulk for reasons of process technology. If necessary because of solubility parameters, the polymerization may, if desired, also be carried out in solution, in particular in the presence of a nonpolar solvent, such as benzene, toluene, xylene, ethylbenzene, n-hexane, cyclohexane, petroleum ether, decalin or a mixture of these. The solution polymerization is also successful in polar aprotic solvents, e.g. in tetrahydrofuran, diethyl ether, dioxane, chloroform, dichloromethane or acetone. If required, the polymeric products may be obtained by adding a precipitating agent, for example a polar protic compound, such as methanol, ethanol or water.

The emulsion polymerization is preferably carried out at from 20 to 90° C. Examples of suitable emulsifiers are block copolymers of ethylene oxide and of propylene oxide, ethoxylated mono-, di- and trialkylphenols (e.g. EO number: from 3 to 50 and alkyl radical: from $C_4$ to $C_9$), ethoxylated fatty alcohols (e.g. EO number: from 3 to 50 and alkyl radical: from $C_8$ to $C_{36}$), and also the alkali metal and ammonium salts of alkyl sulfates (e.g. alkyl radical: from $C_8$ to $C_{30}$), of sulfuric monoesters of ethoxylated alkanols (e.g. EO number: from 4 to 30 and alkyl radical: from $C_{12}$ to $C_{30}$) and of ethoxylated alkylphenols (e.g. EO number: from 3 to 50 and alkyl radical: from $C_4$ to $C_{15}$), of alkylsulfonic acids (e.g. alkyl radical: from $C_{12}$ to $C_{35}$) and of alkylarylsulfonic acids (e.g. alkyl radical: from $C_9$ to $C_{35}$). The class of suitable emulsifiers also includes the sulfosuccinates (sulfosuccinic esters) of $C_8$–$C_{18}$-alkanols, and also the water-soluble salts of these sulfosuccinates, in particular the alkali metal salts, among which the sodium salt is preferred.

Other suitable dispersants are compounds of the formula VIII

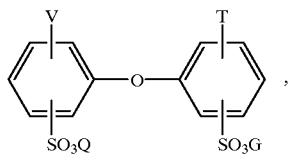

(VIII)

where V and T are hydrogen or $C_4$–$C_{14}$-alkyl, but not simultaneously hydrogen, and Q and G may be alkali metal ions and/or ammonium ions. V and T are preferably linear or branched alkyl radicals having from 6 to 18 carbon atoms, or hydrogen, and in particular having 6, 12 or 16 carbon atoms, where V and T are not both simultaneously hydrogen. Q and G are preferably sodium, potassium or ammonium ions, sodium being particularly preferred. Compounds VIII in which Q and G are sodium, V is branched alkyl having 12 carbon atoms and T is hydrogen or V are particularly advantageous. Use is frequently made of technical mixtures which have a proportion of from 50 to 90% by weight of the mono-alkylated product, for example Dowfax® 2A1 (trademark of Dow Chemical Company). The compounds VIII are generally known, e.g. from U.S. Pat. No. 4,269,749, and are commercially available. According to the invention, it is expedient to select the amount of emulsifier in such a way that the critical micelle-formation concentration of the emulsifiers used is essentially not exceeded in the aqueous phase of the aqueous emulsion to be polymerized. Based on the monomers contained in the emulsion, the amount of emulsifier is generally from 0.1 to 5% by weight. The emulsifiers may, of course, also be accompanied by protective colloids which are capable of stabilizing the disperse distribution of the aqueous polymer dispersion which is finally produced.

For preparing the dispersion, use is in particular made of an amount of water sufficient to give the finished dispersion a solids content of from 20 to 50% by weight. Examples of suitable molecular-weight regulators are ethylhexyl thioglycolate, tert-dodecylmercaptan, terpinols and dimeric α-methylstyrene. A constant pH is generally set using buffer substances, such as $Na_2HPO_4/NaH_2PO_4$ or sodium hydrogencarbonate, and is preferably from 6 to 9. Emulsifiers, initiators, regulators and buffer substances are used in the usual amounts, and it is therefore unnecessary to give further details on this point. Conventional aqueous emulsions suitable for the emulsion polymerization may be produced here in a manner known per se from the constituents of the emulsion.

The novel polymerizations may also be carried out in microemulsion. Microemulsions are obtained from the aqueous emulsions described, generally using high-pressure homogenizers (cf. P. L. Tang et al., J. Appl. Polym. Sci., 1991, 43, pp. 1059–1066) or ultrasound. For details of these processes, the earlier German Application DE-A 19 727 505 is expressly incorporated herein by way of reference. These processes give aqueous emulsions whose disperse phase is composed primarily of droplets having a diameter of ≦500 nm.

The microsuspension polymerization process in which the monomer mixture is dispersed in water in the presence of a protective colloid and with intensive stirring, i.e. with high shear force, may likewise be used. For this, use is usually made of stirrer systems operated at circumferential speeds of from 10 to 25 m/s, or of other dispersion systems. Once the droplets have reached the desired size, the polymerization is undertaken by adding the novel initiator with moderate stirring at circumferential speeds of less than 3 m/s at temperatures of generally from 40 to 130° C.

Examples of suitable protective colloids are cellulose derivatives, such as carboxymethylcellulose and hydroxymethylcellulose, poly-N-vinylpyrrolidione, polyvinyl alcohol and polyethylene oxide, anionic polymers, such as polyacrylic acid, and cationic polymers, such as poly-N-vinylimidazole, in concentrations of preferably from 0.02 to 1% by weight of the total weight of the dispersion.

Particularly good results are achieved if, in addition to the protective colloids, there is concomitant use of colloidal silica in a concentration of generally from 0.2 to 5% by weight, based on the amount of dispersion. Further details of this method, which is particularly successful with a water-soluble polymer made from adipic acid and diethanolamine as protective colloid, can be found in U.S. Pat. No. 3,615, 972. Concomitant use of a water-soluble inhibitor is expedient in order to suppress the emulsion polymerization process which occurs simultaneously during the microsuspension polymerization and forms significantly smaller particles. The inhibitor suppresses the emulsion polymerization. Examples of effective compounds of this type are chromium(+6) compounds, such as potassium dichromate.

The microsuspension polymerization is preferably carried out at a pH of from 3 to 9. Polymerization of the monomers takes place at from 20 to 160° C., preferably from 40 to 130° C. The amount of water is preferably from 40 to 70% by weight of the total amount of dispersion.

For the suspension polymerization, which is likewise possible, that which has been said for the microsuspension polymerization process applies similarly, except that moderate circumferential stirring speeds of less than 5 m/s are used from the beginning.

The (co)polymers which have end groups and are obtained by conventional free-radical polymerization generally have an average of from 1 to 5, preferably from 1 to 2.5, heterocyclic units (VII) per (co)polymer chain. The end-group functionality content can be determined using titration or by quantitative NMR spectroscopic analyses. In general, the polydispersities of these (co)polymers are in the range from 1.1 to 4.0, preferably from 1.1 to 3.0, and the resultant molecular weights $M_w$ are in the range from 3000 to 250,000 g/mol, preferably from 40,000 to 150,000 g/mol. The molecular weight is controllable within wide limits via the ratio of initiator to monomer. Suitable amounts of initiator are in particular in the range from 0.01 to 10% by weight, based on the total amount of monomer used.

It has moreover been found that specific incorporation of only one reactive heterocyclic end group (VII) per polymer chain is successful if the novel polymerization process is carried out under the conditions of controlled free-radical polymerization. Controlled free-radical polymerizations are carried out in the presence of stable free radicals, such as 2,2,6,6-tetramethyl-1-piperidyloxyl (TEMPO) or 2,2,5,5-tetramethyl-1-pyrrolidyloxyl (PROXYL) as described, for example, in the U.S. Pat. Nos. 5,322,912 and 5,401,804, and also in the scientific publications in TRIP 1994, Vol. 2, p. 66–71, Macromolecules, 1995, Vol. 28, p. 6381 and 6382, and Macromolecules, 1995, Vol. 28, pp. 8453–8455.

Reaction times selected for the controlled free-radical polymerization may be from 1 to 50 hours, preferably from 4 to hours, and the ideal reaction time depends, inter alia, on the polymerization temperature, the size of the reaction batch, and the amount of polymerization initiator and also of stable free-radical species. Controlled free-radical polymerization here is generally carried out at from −50 to 160° C., preferably from 60 to 160° C., particularly preferably from 100 to 150° C. and in particular from 115 to 145° C. The polymerization may, of course, also be carried out at temperatures above 160° C. However, this is generally accompanied by a wider molecular weight distribution. It is advantageous to operate with the exclusion of oxygen. Aqueous systems, on the other hand, are tolerated without any difficulty.

Like the conventional free-radical polymerization, the controlled free-radical polymerization may be carried out in solution, suspension or bulk. For reasons of simpler isolation and handling, the polymerization is frequently carried out in bulk if this is not excluded because of solubility parameters or other reaction parameters.

The molar ratio of initiator species to stable free radical is usually in the range from 0.4 to 2.5, preferably in the range from 0.6 to 1.6 and particularly preferably in the range from 0.7 to 1.4. If the amount of stable free radical is excessive, the inhibition of the polymerization reaction may be too powerful, resulting in incomplete conversion and low molecular weights.

The molar ratio of monomer to stable free radical is generally set in a range of from 100:1 to 5000:1 and preferably in a range of from 150:1 to 2000:1.

Possible stable free radicals for the controlled free-radical polymerization are in general organic or inorganic compounds having a stable free NO radical. Organic NO radicals which are sterically hindered have proven particularly successful, for example the 2,2,6,6-tetramethyl-1-piperidinyloxy or 2,2,5,5-tetramethyl-1-pyrrolidinyloxy compounds already mentioned, and also their derivatives. The derivatives include, for example, compounds which are substituted in the 2 and/or 5 (PROXYL) and/or 6 (TEMPO) position by linear or branched, substituted or unsubstituted low-molecular-weight $C_2$–$C_6$-alkyl, such as ethyl, isopropyl, n-butyl, tert-butyl or trifluoromethyl, or by triorganosilyl, such as trimethylsilyl or triisopropylsilyl, or by a functional group, such as carboxyester, nitro or amide. It is also possible for the other carbon atoms of the piperidine or pyrrolidine ring system to be substituted with alkyl or aryl, or with functional groups based on the non-metallic elements of groups IVA, VA, VIA or VIIA of the Periodic Table of the Elements, such as carboxy, nitrile, amino, nitro, hydroxyl, alkoxy or halogen. For example, there may be an amino, hydroxyl, keto or carboxylic acid or ester function in the 4 position of the piperidine ring. Examples which may be mentioned of representatives of suitable stable NO radicals are 4-hydroxy-2,2,6,6-tetramethyl-1-oxylpiperidine, 4-hydroxy-2,6-diphenyl-2,6-dimethyl-1-oxylpiperidine, 4-carboxy-2,2,6,6-tetramethyl-1-oxylpiperidine, 4-carboxy-2,6-diphenyl-2,6-dimethyl-1-oxylpiperidine and the sodium or potassium salt of the sulfuric acid monoester of 4-hydroxy-2,2,6,6-tetramethyl-1-oxylpiperidine. Among the substituted pyrrolidine derivatives, mention may be made of the 3-carboxylic acid, 3-amido, 3-methoxy, 3-tert-butyl and 3-aminomethyl compounds of the 2,2,5,5-tetramethyl-1-pyrrolidinyloxy radical, and also the corresponding 2,5-diphenyl-2,5-dimethyl-1-pyrrolidinyloxy radical compounds. Tetramethyl- and also tetraethylisoindolinyloxy radical compounds are also suitable. Other than these, the stable NO (N-oxyl) radicals described in the earlier German Patent Application DE-A 19 727 505 are expressly incorporated herein by way of reference as stable radicals also suitable in the present case. It is, of course, also possible to use mixtures of stable free NO radicals. The organic NO radicals mentioned are generally known from the literature (see also G. Moad, Tetrahedron Letters, 1981, 22, p. 1165). The preparation of 3-carboxy-2,2,5,5-tetramethyl-1-oxylpyrrolidine can be found, for example, in Romanelli, M.; Ottaviani, M. F.; Martini, G.; Kevan, L., JPCH J: Phys. Chem., EN, 93, 1, 1989, pp. 317–322.

Using controlled free-radical polymerization, it is possible here to obtain homo- and copolymers at high or generally quantitative conversions from monomers capable of free-radical polymerization. In addition, block copolymers of high purity can be obtained by adding different monomers in sequence and allowing them to react to completion. Suitable monomers for preparing homopolymers, copolymers or block copolymers terminated by a reactive end group (VII) are therefore, inter alia, styrene, acrylonitrile, methyl methacrylate, n-butyl acrylate, 2-ethylhexyl acrylate or mixtures of these.

The controlled free-radical polymerization here may be terminated by lowering the temperature. To isolate the products, the crude product obtained is, for example, dissolved in a polar aprotic medium, for example in a low-molecular-weight ether, such as tetrahydrofuran, and the end product is isolated by precipitation in methanol or ethanol.

The homo- and copolymers obtained using free-radical polymerization are suitable for processing to give films, fibers and moldings.

Due to their reactive heterocyclic end group(s), the novel homo- and copolymers are also suitable for downstream reactions, which are generally not based on free-radical mechanisms. The reactivity of the heterocycle may particularly advantageously be utilized to bring about mixing or blending with other polymer components which have a low compatibility or are incompatible. This requires a polymer which has one or more functional groups which are reactive to the heterocycle in the end group (VII). For example, the oxazoline or thiazoline group reacts with a carboxylic acid or anhydride function with ring-opening and development of a (thio)ester unit and also an amide unit as coupling elements for two polymer blocks linked covalently with one another. Possible anhydrides are either noncyclic symmetrical or asymmetrical anhydrides or cyclic anhydrides. Depending on the number of reactive end groups present in the polymer, either pure block copolymers or graft copolymers are possible.

It is possible, for example, to obtain symmetrical (CDC) three-block copolymers whose terminal blocks are based on novel monofunctionalized homo- or copolymers obtainable using controlled free-radical polymerization and whose middle block is a bifunctional, dicarboxylic-acid-terminated fragment. It is therefore possible to obtain, for example, poly[(styrene-co-acrylonitrile)-b-(tetrahydrofuran)-b-(styrene-co-acrylonitrile)] or poly(styrene-b-(polytetrahydrofuran)-b-styrene). It is, of course, also possible in the same way to react an oxazoline-functionalized copolymer of ethane and methyl acrylate with a carboxylic-acid- or anhydride-functionalized polymer. Commercially obtainable carboxylic-acid- and/or anhydride-terminated copolymers, such as Nucrel® (polyethylene methacrylic acid) or Vamac® (carboxylic-acid- and/or maleic-anhydride-functionalized acrylate rubbers) (both products of DuPont) are also suitable for coupling with the novel (co)polymers, i.e. for example with oxazoline-terminated styrene-acrylonitrile copolymer. Finally, acid-terminated polymers are also obtainable via appropriately functionalized azo initiators (see also M. Baumert, R. Mülhaupt, Macromol. Rapid Commun. 1997, 18, 787–794 or JP-A-06093100). The variety of available coupling partners for the (co)polymers functionalized according to the invention is therefore as great as that of the (co)polymers mentioned.

The graft and block copolymers described may be obtained under reactive extrusion conditions, as described in the monograph "Reactive Extrusion, Principles and Practice" by M. Xanthos, Carl Hanser Verlag, Munich, 1992. Use is particularly frequently made of the following functionalized polymer classes: core-shell rubbers based on styrene/butadiene with acrylate shell, e.g. Paraloid® (Rohm & Haas), ethylene/acrylate rubbers, such as Lucalen® (BASF AG), acid-containing polyethylene, such as Nucrel® (DuPont), poly(styrene-co-acrylonitrile), e.g. Luran® (BASF AG), acrylate rubbers, such as polybutyl acrylate, for example the IR series from Mitsubishi-Rayon, polyesters, such as Crastin® (DuPont) or Ultradur® (BASF AG), polyamides, such as Ultramid® (BASF AG), or polycarbonates, such as Apec® (Bayer AG) or Lexan® (GE Plastic).

It is generally possible to react a carboxylic-acid- or anhydride-terminated polymer component and, for example, an oxazoline-terminated polymer component even by simple annealing at from 50 to 300° C., preferably from 100 to 250° C. and particularly preferably from 150 to 220° C., to give covalently bonded two- or multiblock systems or graft copolymers. Depending on the ratio selected of the polymer components reacting with one another, this gives either polymer systems composed of fully bonded polymer or, if the end groups reacting with one another, such as oxazoline and carboxylic acid, are not present in an equimolar ratio or have not reacted to completion with one another, multicomponent systems in which coupled and uncoupled polymer are present alongside one another. Since the linking step here is generally a well defined coupling reaction, such as ester formation, products resulting from side reactions are not found in the polymeric product when the novel block or graft copolymers are prepared. The course of the coupling reaction may be followed satisfactorily using FTIR spectroscopy. The IR bands for the carbonyl vibration of the carboxylic acid and the C=N vibration of the heterocycle decrease continuously during the course of the reaction, and the bands for the carbonyl stretching vibration of the ester and the resonance vibration of the amide are, in contrast, constantly increasing. The appearance of isosbestic points implies that the reactions are free from side reactions. The course of the reaction, and also the result of the coupling reaction, may also be checked with the aid of gel permeation chromatography.

The block and graft copolymers obtained have, inter alia, high heat resistance. They are suitable for producing fibers, films and moldings. They are also suitable as polymeric compatibilizers in preparing blends of otherwise immiscible polymers.

The novel initiator systems are successful in equipping a wide variety of conventional commodity polymers with selectively manipulable functional groups. Depending on the selection of polymerization method, conventional or controlled free-radical, it is possible to set different levels of functionalization. The process described for preparing the novel azo compounds moreover now makes it possible, by a simple preparative method and using low-cost starting materials, to gain access to a wide variety of azo initiators functionalized with heterocycles. Using the proposed reaction extrusion process, moreover, opens up access to block and graft copolymers with improved properties. A further advantage is that the formation of covalent bonds between the functionalized polymer components can take place directly during extrusion and/or during the blending process. This is also termed reactive blending. The novel (co)polymers allow building-block models to be worked out and used as a basis for combining the properties of very different polymers in a controlled manner, without the need to consider compatibility, in order to obtain blends with new and/or improved, tailored properties.

The invention is described in more detail using the following examples.

EXAMPLES

Styrene was stirred overnight over LiAlH$_4$ and then distilled; acrylonitrile was stirred overnight over CaH$_2$ and then distilled. Tetrahydrofuran (THF) and cyclohexane were refluxed for several hours over sodium/benzophenone and then distilled; CHCl$_3$ was eluted through basic Al$_2$O$_3$; dichloromethane (CH$_2$Cl$_2$) was stirred over CaH$_2$ and then distilled. All of the polymerizations were carried out under an atmosphere of argon. 4,4'-Azobis-(4-cyanopentanoic acid) and 2,2,6,6-tetramethyl-1-piperidyloxyl (TEMPO), both products from Fluka, were used without further purification.

A. Preparation of the azo compounds (I)

EXAMPLE 1

Preparation of 2,2'-azobis[2-methyl-N-(2-chloroethyl)propionamide]

Thionyl chloride (50 ml) was added at 0° C. under an atmosphere of inert gas (argon) to a suspension of 2,2'-azobis[2-methyl-N-(2-hydroxyethyl)propionamide] (38.3 g) in dichloromethane (180 ml) over a period of 30 minutes. The mixture was stirred at room temperature for 18 h, and the precipitate which formed was filtered off, suspended in 100 ml of water and stirred for 5 min. The solid was separated off and dried under reduced pressure at room temperature for 24 h (8.9 g). Further product was isolated from the organic phase of the reaction mixture by adding cyclohexane (250 ml) and cooling to 0° C. The precipitate which formed was filtered off, and worked up and isolated as described above (10.8 g). Finally, the remaining organic filtrate was concentrated to low volume. The precipitate which formed was subjected to the procedure described above (7.6 g).

Elemental analysis: $C_{12}H_{22}N_4O_2Cl_2$ (325.24) calc. (found): C, 44.32; (44.50); H, 6.82; (6.93); N, 17.32; (17.55);

$^1$H NMR (CDCl$_3$): δ=7.3 (s, (O=O)—NH—, 2H); 3.7 (m, NH—CH$_2$—CH$_2$—Cl, 8H); 1.3 (s, (CH$_3$)$_2$—C, 12H); δ=174.0 ((O=C)—NH; 74.8 ((CH$_3$)$_2$—C—); 44.1 (—CH$_2$—Cl); 40.9 (NH—CH$_2$—); 23.0 ((CH$_3$)$_2$—C)).

EXAMPLE 2

Preparation of 2,2'-azobis[2-(1,3-oxazoline)propane]

A solution of 2,2'-azobis[2-methyl-N-(2-chloroethyl) propionamide] (2.0 g) in methanol (10 ml) was added at room temperature to potassium hydroxide (1.73 g) in methanol (20 ml) over a period of min. After 6 days at room temperature, the reaction mixture was filtered through silica gel, the filtrate concentrated to dryness, and the solid taken up in chloroform (20 ml). The resultant mixture was freed from insoluble fractions by filtration, and the filtrate was concentrated under reduced pressure. The final residues of solvent were removed at room temperature and very low pressure giving a yield of 1.0 g.

Elemental analysis: $C_{12}H_{20}N_4O_2$ (252, 16) calc. (found): C, 57.12; (57.21) H, 7.99; (8.05) N, 21.20; (21.54);

IR: ν[cm$^{-1}$]=1645 (C=N), 1250 (C—O), 970, 920, 890;

$^1$H NMR (CDCl$_3$): δ=4.3 (t, CH$_2$—N, 4H); 3.9 (t, CH$_2$—O, 4H); 1.5 (s, (CH$_3$)$_2$—C, 12H);

$^{13}$C NMR (CDCl$_3$); δ=169.9 (O—C=N); 70.3 ((CH$_3$)$_2$—C—); 67.8 (CH$_2$—N); 54.3 (CH$_2$—O); 23.2 ((CH$_3$)$_2$—C).

EXAMPLE 3

Preparation of the 5-(1,3-oxazolin-2-yl)pentyl ester of 4,4'-azobis-4-cyanopentanoic acid 4,4'-Azobis-4-cyanopentanoic acid (1.403 g) and 2-(hydroxypentyl)-1,3-oxazoline (1.732 g) were dissolved in 10 ml of tetrahydrofuran (THF) and then mixed with 25 ml of dichloromethane. 0.070 g of dimethylaminopyridine and 2.272 g of dicyclohexylcarbodiimide were added at 0° C. to the solution. After 4 hours, the reaction mixture was filtered through silica gel, concentrated and freed from the last residues of solvent under suction from an oil pump at room temperature for 24 hours. Slight urea contamination remained in the product.

$^1$H NMR (CDCl$_3$) δ=4.22 (t, CH$_2$—N (ring), 4H); 4.11 (t, (O=C)—O—CH$_2$—, 4H); 3.84 (t,CH$_2$—O (ring), 2.5 (m, (CH$_3$)C(CN)—CH$_2$—CH$_2$—(C=O, 8H); 2.29 (t, —CH$_2$-oxazoline, 4H); 1.6 ((CH$_3$)C(CN) and CH$_2$—CH$_2$—CH$_2$, 18H);

$^{13}$C NMR (CDCl$_3$); δ=168.27 (N=C—O (ring)); 117.49 (CN); 71.94 (CH$_3$)C(CN); 67.20 (CH$_2$—N (ring)); 64.99 ((O=C)—O—CH$_2$—); 54.37 (CH$_2$—O (ring)); 34.93—CH$_2$—(C=O)); 33.20 ((CO=O)—O—CH$_2$—CH$_2$); 30.93 ((CH$_3$)C(CN)—CH$_2$); 27.78 (—CH$_2$-oxazoline); 25.56, 25.53 ((O=C)—O—CH$_2$—CH$_2$—CH$_2$—; 23.99 ((CH$_3$)C (CN).

B. Polymerization process

EXAMPLE 4

Conventional Free-radical Polymerization of Styrene 2,2'-Azobis[2-(1,3-oxazoline)propane] (0.090 g) was dissolved in 40 ml of styrene. To remove the last traces of oxygen, the solution was frozen and then heated to 70° C. After 170 minutes, the polymerization was terminated by lowering the temperature to room temperature, and by adding THF. Two precipitations from methanol gave a colorless powder, which was dried at room temperature for 24 hours using the suction from an oil pump.

Yield: 8.91 g of polystyrene; $M_n$=49,000 g/mol; $M_w$=84,100 g/mol; $M_w/M_n$=1.72.

EXAMPLE 5

Controlled Free-radical Polymerization of Styrene

TEMPO (0.116 g) and 2,2'-azobis[2-(1,3-oxazoline) propane] (0.188 g) were dissolved in 20 ml of styrene. To remove the last traces of oxygen, the solution was frozen, and then reacted at 140° C. After 12 h at this temperature, the reaction mixture was allowed to cool to room temperature and mixed with 50 ml of THF. The solution of the polymer was accelerated by using ultrasound (Bronsonic B 220; 48 KHz). The final product was precipitated from methanol (500 ml), filtered and freed from the last residues of solvent at 60° C. in a vacuum drying cabinet for 24 h; yield: 15.3 g.

EXAMPLE 6

TEMPO (0.191 g) and the 5-(1,3-oxazolin-2-yl)pentyl ester of 4,4'-azobis-4-cyanopentanoic acid (0.646 g) were dissolved in 33.8 ml of styrene. To remove the last traces of oxygen, the solution was frozen, then reacted at 140° C. After 10 h 15 min at this temperature, the reaction mixture was allowed to cool to room temperature, and mixed with 50 ml of THF. Solution of the polymer was accelerated by using ultrasound (Browonic B220; 48 KHz). The final product was precipitated from methanol (1l), filtered and freed from the last residues of solvent at 60° C. in a vacuum drying cabinet for 24 h. Yield: 17.6 g.

EXAMPLE 7

Conventional Free-radical Azeotropic Copolymerization of Styrene and Acrylonitrile 2,2'-Azobis[2-(1,3-oxazoline)propane] (76 mg) was dissolved in 20 ml of styrene and 8.3 ml of acrylonitrile, degassed by freezing, and heated to 60° C. for 30 minutes. The viscous solution was dissolved in 50 ml of THF, and precipitated from methanol (500 ml). After 24 h at 60° C. at very low pressure, the product obtained was an oxazoline-terminated polystyrene-co-acrylonitrile) in the form of a colorless powder; yield: 7.8 g.

EXAMPLE 8

Controlled Free-radical Azeotropic Copolymerization of Styrene and Acrylonitrile TEMPO (0.559 g) and 2,2'-azobis[2-(1,3-oxazoline) propane] (0.696 g) were dissolved in 72.2 ml of styrene and 30.0 ml of acrylonitrile, degassed by freezing, and held at 120° C. for 8 h. After cooling to room temperature, the reaction mixture was mixed with 150 ml of THF, and the solution process was promoted by using ultrasound. The final product was precipitated from methanol (3l). Filtration, and the removal of the last residues of solvent at 60° C. and very low pressure for 24 h gave a white powder. Yield: 68.7 g.

C. Preparation of block copolymers

EXAMPLE 9

Monocarboxylic-acid-terminated polystyrene (1.5 g) (obtained as specified in M. Baumert, R. Mülhaupt, Macromol. Rapid Commun. 1997, 18, 787–794) was mixed with monooxazoline-terminated styrene-acrylonitrile copolymer (3 g) (obtained as in Example 8), and annealed at 200° C. for 40 min. The course of the reaction was studied by FTIR spectroscopy using a Bruker IFS 88. The result of this series of measurements is given in diagrams 1 and 2 below (difference spectra). At the start of the annealing spectra were taken each minute, and then every five minutes.

We claim:

1. A heterocycle-functionalized azo compound of the formula (I)

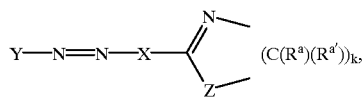

where:

Y is $C_1$–$C_{10}$-alkyl, $C_6$–$C_{10}$-aryl, ester-, amide-, nitrile-, triorganosilyl-, amino-, phosphino-, hydroxyl-, alkoxy-, or fluorine- or chlorine-substituted $C_6$–$C_{10}$-aryl, $C_5$–$C_8$-cycloalkyl, aralkyl having from 1 to 6 carbon atoms in the alkyl radical and from 6 to 10 carbon atoms in the aryl radical, ester-, amide-, nitrile-, triorganosilyl-, amino-, phosphino-, hydroxyl-, alkoxy-, or fluorine- or chlorine-substituted $C_1$–$C_{10}$-alkyl, or a radical of the formula (II)

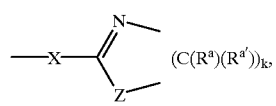

where, as in formula I:

$R^a$ and $R^{a'}$, independently of one another, are hydrogen, $C_1$–$C_{10}$-alkyl, $C_6$–$C_{10}$-aryl, aralkyl having from 1 to 16 carbon atoms in the alkyl radical and from 6 to 10 carbon atoms in the aryl radical, or $C_5$–$C_8$-cycloalkyl, or, but not both simultaneously, ester groups, amide groups, nitrile groups, triorganosilyl, amino, phosphino, hydroxyl, alkoxy, or fluorine or chlorine, Z is oxygen or sulfur, X is —$(C(R^b)(R^{b'}))_l$— or (=N)—$(C(R^b)(R^{b'}))_m$—A—$(C(R^b)(R^{b'}))_n$—$(E)_p$—, where $R^b$ and $R^{b'}$, independently of one another, are defined as for $R^a$ and $R^{a'}$, A is —C(O)O—, —O—, —S—, —C(O)N(R")—, —N(R")—, —C(O)—, —C(R")=N—, E is 1,2-, 1,3- or 1,4-phenylene, unsubstituted or substituted with ester groups, amide groups, nitrile groups, triorganosilyl, amino, phosphino, hydroxyl, alkoxy, or fluorine or chlorine, R' and R" are hydrogen, alkyl, aryl or aralkyl, k is 2 or 3, l is an integer from 1 to 24, m and n are integers from 0 to 1, and p is 0, 1, 2 or 3, where m+n≧1 and n+p≧1.

2. A heterocycle-functionalized azo compound as claimed in claim 1, where the azo compound is a compound of the formula (III)

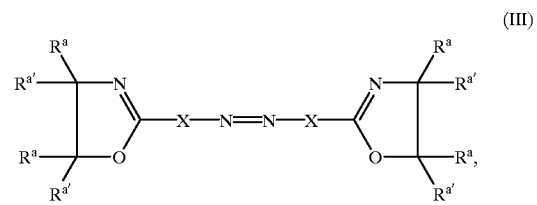

where:

$R^a$ and $R^{a'}$ are hydrogen or methyl,

X, independently of one another, are (=N)—$((C(R^b)(R^{b'}))(C(R^c)(R^{c'}))_{l-1})$— or (=N)—$((C(R^b)(R^{b'}))(C(R^c)(R^{c'}))_{m-1})$—A—$(C(R^c)(R^{c'}))_n$—$(E)_p$— where A is —C(O)O—, —C(O)—, —O—, —C(O)N(R")—, E is 1,4-phenylene, unsubstituted or substituted with ester groups, amide groups, nitrile groups, triorganosilyl, amino, phosphino, hydroxyl, alkoxy, or fluorine or chlorine, $R^b$ is $C_1$–$C_{10}$-alkyl, $R^{b'}$ is an electron withdrawing group, R" is hydrogen, alkyl, aryl or aralkyl, $R^c$ and $R^{c'}$ are hydrogen, $C_1$–$C_{10}$-alkyl, $C_6$–$C_{10}$-aryl or alkylaryl having from 1 to 6 carbon atoms in the alkyl moiety and from 6 to 10 carbon atoms in the aryl moiety, l is from 1 to 6, m and n are from 0 to 7, and p is 0, 1, 2 or 3, where m+n≧1 and n+p≧1.

3. A heterocycle-functionalized azo compound as claimed in claim 2, wherein $R^5$ is selected from the group consisting of —CN, —$CH_3$ and —$CO_2R'''$ where R''' is hydrogen, alkyl, aryl or aralkyl.

4. A process for preparing heterocycle-functionalized azo compounds as claimed in claim 1, which comprises using a halogenating agent in a polar aprotic solvent at a temperature in the range from −20 to 100° C. to convert a compound of the formula (IIIa)

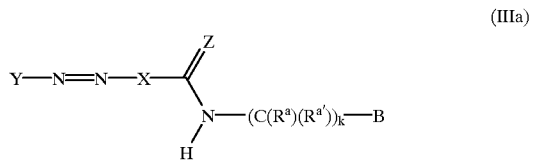

where:

Y is $C_1$–$C_{10}$-alkyl, $C_6$–$C_{10}$-aryl, ester-, amide-, nitrile-, triorganosilyl-, amino-, phosphino-, hydroxyl-, alkoxy-, or fluorine- or chlorine-substituted $C_6$–$C_{10}$-aryl, $C_5$–$C_8$-cycloalkyl, aralkyl having from 1 to 6 carbon atoms in the alkyl radical and from 6 to 10 carbon atoms in the aryl radical, ester-, amide-, nitrile-, triorganosilyl-, amino-, phosphino-, hydroxyl-, alkoxy-, or fluorine- or chlorine-substituted $C_1$–$C_{10}$-alkyl, or a radical of the formula (IV)

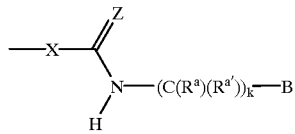

(IV)

where, as in formula IIIa:

$R^a$ and $R^{a'}$, independently of one another, are hydrogen, $C_1$–$C_{10}$-alkyl, $C_6$–$C_{10}$-aryl, aralkyl having from 1 to 6 carbon atoms in the alkyl radical and from 6 to 10 carbon atoms in the aryl radical, or $C_5$–$C_8$-cycloalkyl, or, but not both simultaneously, ester groups, amide groups, nitrile groups, triorganosilyl, amino, phosphino, hydroxyl, alkoxy, or fluorine or chlorine, Z is oxygen, sulfur or —N(R')—, X is —$(C(R^b)(R^{b'}))_l$— or $[=N]$—$(C(R^b)(R^{b'}))_m$—A—$(C(R^b)(R^{b'}))_n$—$(E)_p$—, where $R^b$ and $R^{b'}$, independently of one another, are defined as for $R^a$ and $R^{a'}$, A is —C(O)O—, —O—, —S—, —C(O)N(R")—, —N(R")—, —C(O)—, —C(R")=N—, E is 1,2-, 1,3- or 1,4-phenylene, unsubstituted or substituted with ester groups, amide groups, nitrile groups, triorganosilyl, amino, phosphino, hydroxyl, alkoxy, or fluorine or chlorine, R' and R" are hydrogen, alkyl, aryl or aralkyl, k is 2 or 3, l is an integer from 1 to 24, m and n are integers from 0 to 7, and p is 0, 1, 2 or 3, where m+n≧1 and n+p≧1, and B is hydroxyl, mesyl, trifluoromethylsulfonyl, tosyl or brosyl, into a compound of the formula (IIIb), in which B is Cl, Br or I, and, when the product has been isolated, treating the same with a base in a polar protic solvent at from 0 to 50° C.

5. A process as claimed in claim 4, wherein the halogenation step is excluded and a compound of the formula (IIIa) in which B is mesyl, trifluoromethylsulfonyl, tosyl or brosyl, is treated with a base in a polar protic solvent at from 0 to 50° C.

6. A process for preparing (co)polymers containing heterocyclic end groups, which comprises free-radical polymerization of olefinically unsaturated compounds in the presence of a heterocycle-functionalized azo compound as claimed in claim 1.

7. A process as claimed in claim 6, wherein the free-radical polymerization is carried out in the presence of a stable free NO radical.

8. A (co)polymer product obtained from the process as claimed in claim 6.

9. A process for preparing graft copolymers or block copolymers, which comprises reacting the (co)polymers obtained as claimed in claim 6 with polymer chains or oligomer chains which contain carboxylic acid groups or carboxylic anhydride groups.

10. A graft copolymer or a block copolymer obtained by the process as claimed in claim 9.

11. Films, fibers or moldings produced from the graft copolymer or block copolymer as claimed in claim 10.

12. A process for the free-radical polymerization of olefinically unsaturated compounds, wherein the initiator is the heterocycle-functionalized azo compound as claimed in claim 1.

13. A process for the production of block copolymers or graft copolymers which comprises reacting (co)polymers as claimed in claim 8 with one or more polymers having functional groups capable of reacting with the heterocyclic end group or groups of said (co)polymers.

14. The process as claimed in claim 16, wherein said functional groups are carboxylic acid groups or carboxylic anhydride groups.

* * * * *

UNITED STATES PATENT AND TRADEMARK OFFICE
CERTIFICATE OF CORRECTION

PATENT NO. : 6,313,275 B1
DATED : November 6, 2001
INVENTOR(S) : Muehlhaupt et al.

It is certified that error appears in the above-identified patent and that said Letters Patent is hereby corrected as shown below:

Column 18,
Lines 6 and 42, "p is0, 1, 2 or 3," should be -- p is 0, 1, 2 or 3, --;
Line 45, "$R^5$" should be -- $R^{b'}$ --;
Line 46, "-$CH_3$" should be -- -$CF^3$ --.

Column 20,
Line 38, "16" should be -- 13 --.

Signed and Sealed this

Tenth Day of December, 2002

JAMES E. ROGAN
*Director of the United States Patent and Trademark Office*